(12) United States Patent
Takatsuka

(10) Patent No.: US 8,149,403 B2
(45) Date of Patent: Apr. 3, 2012

(54) OPTICAL EQUIPMENT HAVING WAVELENGTH-INDEPENDENT OPTICAL PATH DIVISION ELEMENT

(75) Inventor: Hirofumi Takatsuka, Tokyo (JP)

(73) Assignee: Olympus Corporation, Tokyo (JP)

( * ) Notice: Subject to any disclaimer, the term of this patent is extended or adjusted under 35 U.S.C. 154(b) by 444 days.

(21) Appl. No.: 12/388,587

(22) Filed: Feb. 19, 2009

(65) Prior Publication Data

US 2009/0213376 A1 Aug. 27, 2009

(30) Foreign Application Priority Data

Feb. 22, 2008 (JP) ................................ 2008-041788

(51) Int. Cl.
*G01J 4/00* (2006.01)

(52) U.S. Cl. ...................................................... 356/364

(58) Field of Classification Search ............ 356/364–370
See application file for complete search history.

(56) References Cited

U.S. PATENT DOCUMENTS

| | | | |
|---|---|---|---|
| 2002/0030807 A1* | 3/2002 | Maeda et al. | 356/237.2 |
| 2005/0111516 A1* | 5/2005 | Hatano et al. | 372/106 |
| 2006/0158624 A1* | 7/2006 | Toyoda | 355/18 |
| 2007/0183040 A1* | 8/2007 | Sinyugin et al. | 359/515 |

FOREIGN PATENT DOCUMENTS

JP 2003-021788 A 1/2003

* cited by examiner

*Primary Examiner* — Gregory J Toatley
*Assistant Examiner* — Tara S Pajoohi
(74) *Attorney, Agent, or Firm* — Holtz, Holtz, Goodman & Chick, PC

(57) ABSTRACT

Optical equipment for detecting beams emitted from a sample by irradiating the sample with linear polarization according to an aspect of the present invention includes a wavelength-independent optical path division element arranged at a position of coupling of a illumination optical path of the linear polarization and a detection optical path of the beams, and the linear polarization is reflected by the interface of the optical path division element entered as S polarization and led to the sample, and the beams pass through the optical path division element and are detected.

24 Claims, 4 Drawing Sheets

OPTICAL EQUIPMENT HAVING WAVELENGTH-INDEPENDENT OPTICAL PATH DIVISION ELEMENT

CROSS REFERENCE TO RELATED APPLICATIONS

This application is based upon and claims the benefit of priority from the prior Japanese Patent Application No. 2008-041788, filed Feb. 22, 2008, the entire contents of which are incorporated herein by reference.

BACKGROUND OF THE INVENTION

1. Field of the Invention

The present invention relates to the technology of optical equipment, and more specifically to the technology of separating beams.

2. Description of the Related Art

Optical equipment such as a microscope etc. uses a dichroic mirror as means for separating beams. A dichroic mirror refers to an optical element having different transmittance (that is, reflectance) depending on the wavelength, and the beams entering the optical element are separated into predetermined beams.

For example, a fluorescent microscope uses a dichroic mirror in separating beams into fluorescence and excitation light. The wavelength of fluorescence tends to be longer than the wavelength of excitation light (referred to as a Stokes' shift). To separate beams by taking the advantage of the characteristic, a dichroic mirror is arranged at the position of coupling the optical path of excitation light (illumination optical system) to the optical path of fluorescence (observation optical system).

However, the wavelength of fluorescence and the wavelength of excitation light depend on the fluorescence substance to be used. In many cases, plural fluorescence substances are combined for use. Therefore, the optimum dichroic mirror is to be selected for each observation performed. To attain this, a number of dichroic mirrors are to be prepared, which means an increasing cost and an upsized and more complicated device. In addition, exchanging dichroic mirrors requires some time, which is the problem in an observation requiring management of time with high accuracy during observation such as a high-speed observation.

Relating to the above-mentioned problem, Japanese Published Patent Application No. 2003-21788 discloses the technology using a non-coated glass (or using a reflection preventive coat to adjust reflectance) instead of a dichroic mirror as means for separating beams. In this method, since normal optical glass including the non-coated glass substantially is wavelength-independent, it is not necessary to exchange means for separating beams for each fluorescence substance.

SUMMARY OF THE INVENTION

The optical equipment for detecting beams emitted from a sample by irradiating the sample with linear polarization according to an aspect of the present invention includes a wavelength-independent optical path division element arranged at a position of coupling of a illumination optical path of the linear polarization and a detection optical path of the beams, and the linear polarization is reflected by the interface of the optical path division element entered as S polarization and led to the sample, and the beams pass through the optical path division element and are detected.

BRIEF DESCRIPTION OF THE DRAWINGS

The present invention will be more apparent from the following detailed description when the accompanying drawings are referenced.

DESCRIPTION OF THE PREFERRED EMBODIMENTS

The embodiments of the present invention are described below with reference to the attached drawings.

Embodiment 1

Figure 1:
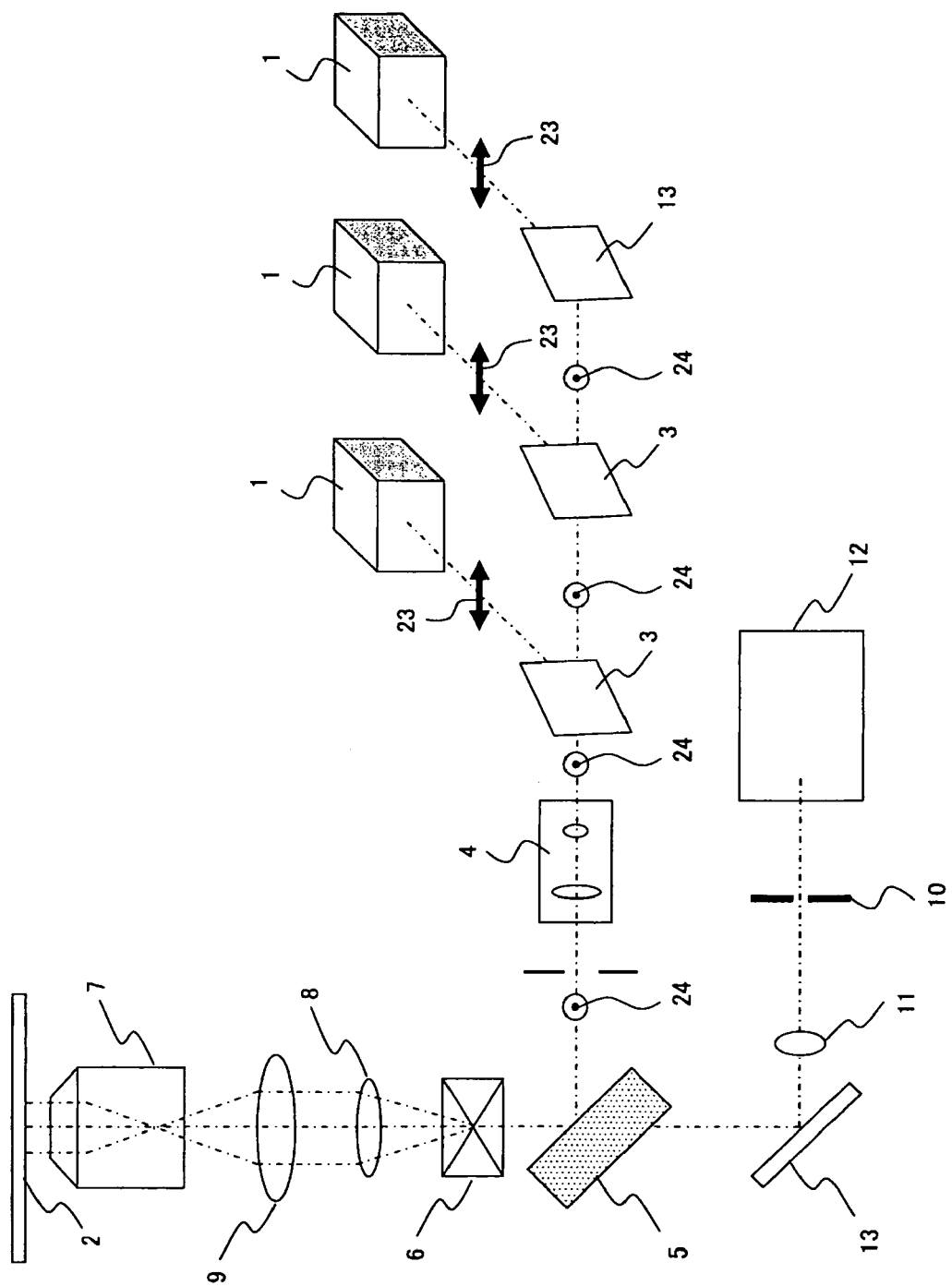
FIG. 1 shows the outline of the configuration of the laser scanning microscope according to an embodiment of the present invention.

FIG. 1 shows the outline of an example of the configuration of the laser scanning microscope as optical equipment for embodying the present invention. Especially, the laser scanning microscope shown in FIG. 1 uses a sample in which a fluorescence substance is introduced or realized, excites the fluorescence substance by laser beams, and observes the fluorescence. The laser scanning microscope according to the present embodiment is smaller and more concise than a common laser scanning microscope. That is, the entire optical equipment realizes the characteristics of the effect of the present invention, that is, concise and small equipment.

In the present embodiment, a plurality of laser diodes (LDs) are used as a laser beam source 1. The laser beams from the laser beam source 1 reach a sample surface 2 without optical fiber. In a common laser scanning microscope, a laser unit is separated from a microscope unit, and they are connected through optical fiber. The configuration not only causes a loss in the intensity of laser beams, but also generates a larger device. Therefore, the laser scanning microscope according to the present embodiment has the configuration without optical fiber.

The laser beams from a laser diode normally have oval sections. However, the direction of the major axis of the section of a laser beam does not necessarily match the polarization surface of the laser beam. Therefore, a configuration of matching the direction of the major axis of the section of a laser beam and the polarization surface of the laser beam is devised. For example, a λ/2 plate can be arranged near the outlet of the laser diode 1 to rotate the polarization surface and match the direction of the major axis of the laser beam and the polarization surface. Such a device is effective in avoiding the interference by the back-surface reflection of laser beams described later in detail.

Practically, the laser scanning microscope according to the present embodiment is configured by the laser beam source 1 for emitting laser beams, a dichroic mirror 3 for combining the laser beams, a beam expander 4 for expanding the luminous flux of the laser beams, a plane-parallel plate glass 5 for reflecting and introducing the laser beams to a detection optical path, a galvano mirror 6 for scanning the laser beams and fluorescence, a pupil projection lens 8 for projecting the pupil of the objective lens 7 to the galvano mirror 6, a tube lens 9 for forming beams from a sample into an image as a pair to the objective lens 7, a confocal lens 11 for condensing the fluorescence that has passed the plane-parallel plate glass 5 to a confocal pinhole 10, and a detector 12 for detecting the fluorescence that has passed the confocal pinhole 10. A mirror 13 shown in FIG. 1 is to appropriately arrange the optical path.

It is desired that the plane-parallel plate glass 5 is double-sided and non-coated optical glass. Optical glass is clear, but has appropriate reflectance. Therefore, the plane-parallel plate glass 5 takes advantage of the reflectance to function as an optical path division element.

In addition, the wavelength-dependency of the optical glass itself is much lower than the wavelength-dependency of the dichroic mirror. Therefore, in the present specification, the plane-parallel plate glass 5 made of the optical glass has no wavelength-dependency of normal optical glass. That is, it is considered that the plane-parallel plate glass 5 is wavelength-independent.

With the above-mentioned configuration, the laser beams from a plurality of laser beam sources 1 enter the dichroic mirror 3 as P polarization, and pass and reflect on the dichroic mirror 3. Thus, the laser beams emitted from the laser beam sources 1 are combined into a bundle of laser beams. Then, the luminous flux of the combined laser beams is expanded by the beam expander 4, and enters the plane-parallel plate glass 5. The plane-parallel plate glass 5 reflects the laser beams, and leads the reflected light in the direction of the objective lens 7. At this time, expanding the luminous flux by the beam expander 4 works for downsizing the optical system between the beam expander 4 and the laser beam sources 1. That is, by reducing the diameter of the luminous flux, the dichroic mirror 3 can be downsized. Additionally, the laser beam sources 1 and the peripheral optical elements can be easily arranged.

In this case, the laser beams emitted from the beam expander 4 are made to enter the plane-parallel plate glass 5 as S polarization because the reflectance of the S polarization is different from that of P polarization, and the reflectance of the S polarization is higher. Generally, P polarization has an incident angle corresponding to the reflectance of 0, and the angle is referred to as a Brewster's angle. Normally, the angle is about 56 degrees. In the present configuration, the laser beams are emitted at the incident angle of 45° to the plane-parallel plate glass 5. At the incident angle, the difference between the S polarization and the P polarization is large. Therefore, to efficiently obtain reflected light, the laser beams are emitted as S polarization. When the refractive index of the glass is n, the Brewster's angle is assigned by Arctan (n). Accordingly, by using a lower refractive index of the plane-parallel plate glass 5, the Brewster's angle can be closer to 45°.

The configuration of allowing the laser beams to enter the dichroic mirror 3 as P polarization when they pass through or are reflected by the dichroic mirror 3 is effective in downsizing the optical equipment and in a efficient use of the laser beams. Since a sample is horizontally arranged, the objective lens 7 is arranged with its optical axis directed in the perpendicular direction relative to the sample. Hereinafter, according to the present specification, the direction parallel to the surface on which a sample is placed is referred to as a horizontal direction, and the direction parallel to the surface including the optical axis of the objective lens is referred to as a vertical direction. That is, the optical path from the objective lens 7 to the plane-parallel plate glass 5 is configured as compact as possible and not to interpose any reflecting member such as a mirror etc., the optical path from the plane-parallel plate glass 5 to the dichroic mirror 3 is horizontally configured. That is, to allow the laser beams to enter plane-parallel plate glass 5 as the S polarization, it is the most natural to also horizontally place the polarization surface of the laser beams between the plane-parallel plate glass 5 and the dichroic mirror 3. On the other hand, it is desired that the laser beam sources 1 are horizontally arranged. In this case, the laser beams are also arranged horizontally. Therefore, to horizontally configure the polarization surfaces of the laser beams between the plane-parallel plate glass 5 and the dichroic mirror 3, it is the most natural to allow the laser beams to enter the dichroic mirror 3 as the P polarization. That is, according to the present embodiment, the laser beams enter the plane-parallel plate glass 5 as the S polarization, and enter the dichroic mirror 3 as the P polarization. With the configuration, it is possible to realize both efficient use of the laser beams and entirely downsized optical equipment.

Polarization direction is distinguished by using the symbol which shows polarization direction 23 and the symbol which shows polarization direction 24 in FIG. 1.

Fluorescence is emitted from a fluorescence substance in a sample excited by laser beams, and the fluorescence is generally random polarization. That is, the fluorescence emitted from the sample surface is not S polarization when entering the plane-parallel plate glass 5 through the objective lens 7, the tube lens 9, the pupil projection lens 8, and the galvano mirror 6. Therefore, the fluorescence can be efficiently transmitted through the plane-parallel plate glass 5 without the influence of an increased reflectance of the plane-parallel plate glass 5 by the polarization characteristic.

The fluorescence that has passed through the plane-parallel plate glass 5 is condensed to the confocal pinhole 10 by the confocal lens 11. At this time, the confocal pinhole 10 and the sample surface 2 have optical conjugate relationship, and the beams from a point other than the sample surface are cut off by the confocal pinhole 10. As a result, the laser scanning microscope of this configuration has a so-called sectional effect (also referred to as a confocal effect).

The fluorescence that has passed the confocal pinhole 10 is detected by the detector 12, and is imaged by the image processing device not shown in the attached drawings. In the present embodiment, the fluorescence that has passed the confocal pinhole 10 is simply detected, but it is also possible to further include a spectral device for measuring the spectrum of the detected fluorescence.

In the present embodiment, a device is designed for the thickness of the plane-parallel plate glass 5. Generally, a phenomenon referred to as back-surface reflection occurs on an optical element. Especially an element having the shape of a plane-parallel plate such as a filter etc. has a large influence of back-surface reflection. Additionally, according to the present embodiment, since the transmittance on the surface of the plane-parallel plate glass 5 is high, the quantity of light of the back-surface reflection is large. Therefore, according to the present embodiment, the influence of the back-surface reflection is removed by thickening the plane-parallel plate glass 5.

Figure 2:
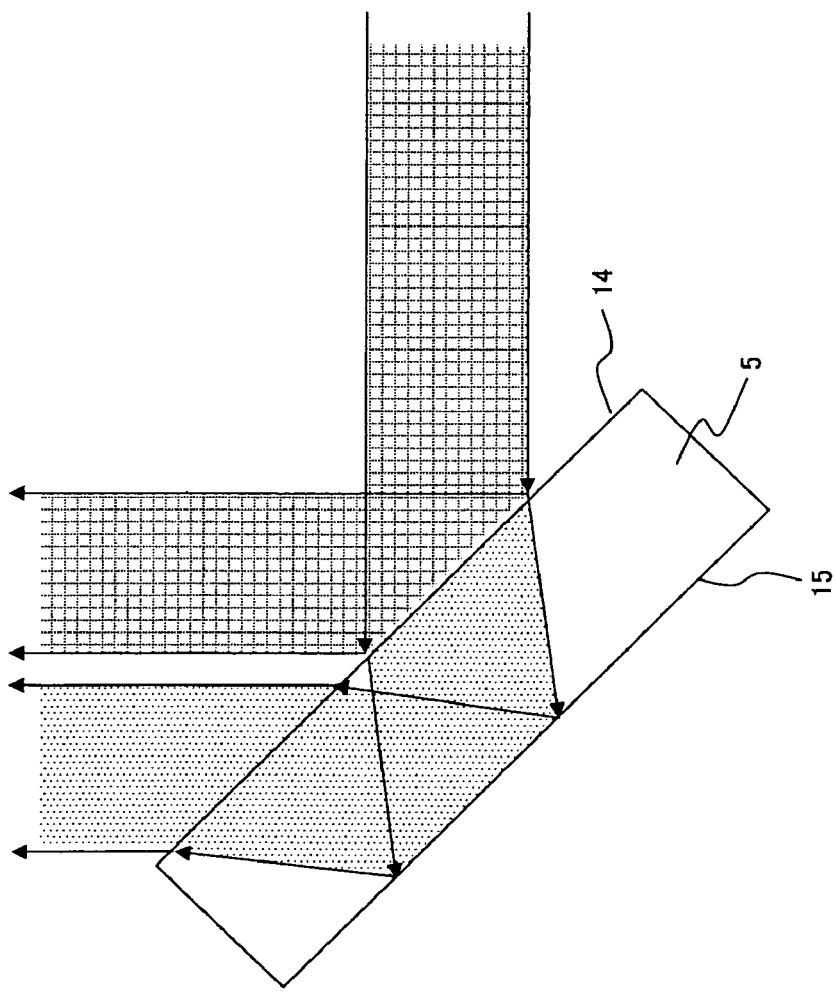
FIG. 2 is an explanatory view of the back-surface reflection on plane-parallel plate glass.

FIG. 2 is an explanatory view of the configuration of removing the beams of the back-surface reflection on the plane-parallel plate glass 5 from the regular optical path. The beams of the regular optical path (grid area shown in FIG. 2) are reflected by a surface 14 of the plane-parallel plate glass 5, and led to the sample surface. On the other hand, the beams of the optical path of the back-surface reflection (in the dotted area shown in FIG. 2) are refracted by the surface 14 of the plane-parallel plate glass 5, transmit through the plane-parallel plate glass 5, and are reflected by the back-surface 15 of the plane-parallel plate glass 5.

As shown in FIG. 2, the optical path of the back-surface reflection depends on the luminous flux diameter A of the regular optical path, the thickness D of the plane-parallel plate glass 5, and the refractive index n of the plane-parallel plate glass 5. At this time, the condition of the optical path of the back-surface reflection not crossing the regular optical path is expressed by the following inequality.

$$D > A(n^2 - 0.5)^{1/2}$$

That is, by thickening the plane-parallel plate glass 5 to satisfy the inequality, and cutting off through an iris etc. the excess light by the back-surface reflection, the influence of the back-surface reflection can be suppressed. As indicated by the inequality, reducing the refractive index of the plane-parallel plate glass 5 is preferable because it allows the plane-parallel plate glass 5 not to be excessively thickened. Thus, the space for arrangement of the plane-parallel plate glass 5 can be easily reserved. In addition, if the beams having a Gaussian intensity distribution such as laser beams are used, the central intensity of $1/e^2$ is defined as a luminous flux diameter. Otherwise, an iris is to be mounted at the stage before the plane-parallel plate glass 5, and its diameter can be defined as a luminous flux diameter. With the configuration of the direction of polarization matching the direction of the major axis of the section of the luminous flux, the length of the minor axis can be used as a luminous flux diameter A. That is, interference can be avoided even when a thinner plane-parallel plate glass 5 is used.

In addition, it is also effective to suppress the influence of back-surface reflection by applying a reflection preventive coat to the back-surface 15 of the plane-parallel plate glass 5. When the reflection preventive coat is applied to the back-surface 15 of the plane-parallel plate glass 5, the smaller quantity of light can be required by the reflection by the back-surface 15 than by the surface 14. Thus, the influence of the back-surface reflection can be suppressed. In this case, the surface 14 of the plane-parallel plate glass 5 is not covered with a reflection preventive coat, that is, non-coated.

Another aspect of the method of suppressing the influence of back-surface reflection is to provide a wedge for the plane-parallel plate glass. That is, an angle is made between the surface 14 and the back-surface 15 of the plane-parallel plate glass 5. With the device, the beams of back-surface reflection are reflected at an angle quite different from the beams of surface reflection. Therefore, by appropriately setting the distance to the next optical element (galvano mirror 6 in the present embodiment), the beams of the back-surface reflection can be led to the outside of the regular optical path. Furthermore, the plane-parallel plate glass can be replaced with a prism-shaped optical path division element to obtain an effect similar to the wedge provided for the plane-parallel plate glass.

Embodiment 2

Figure 3:
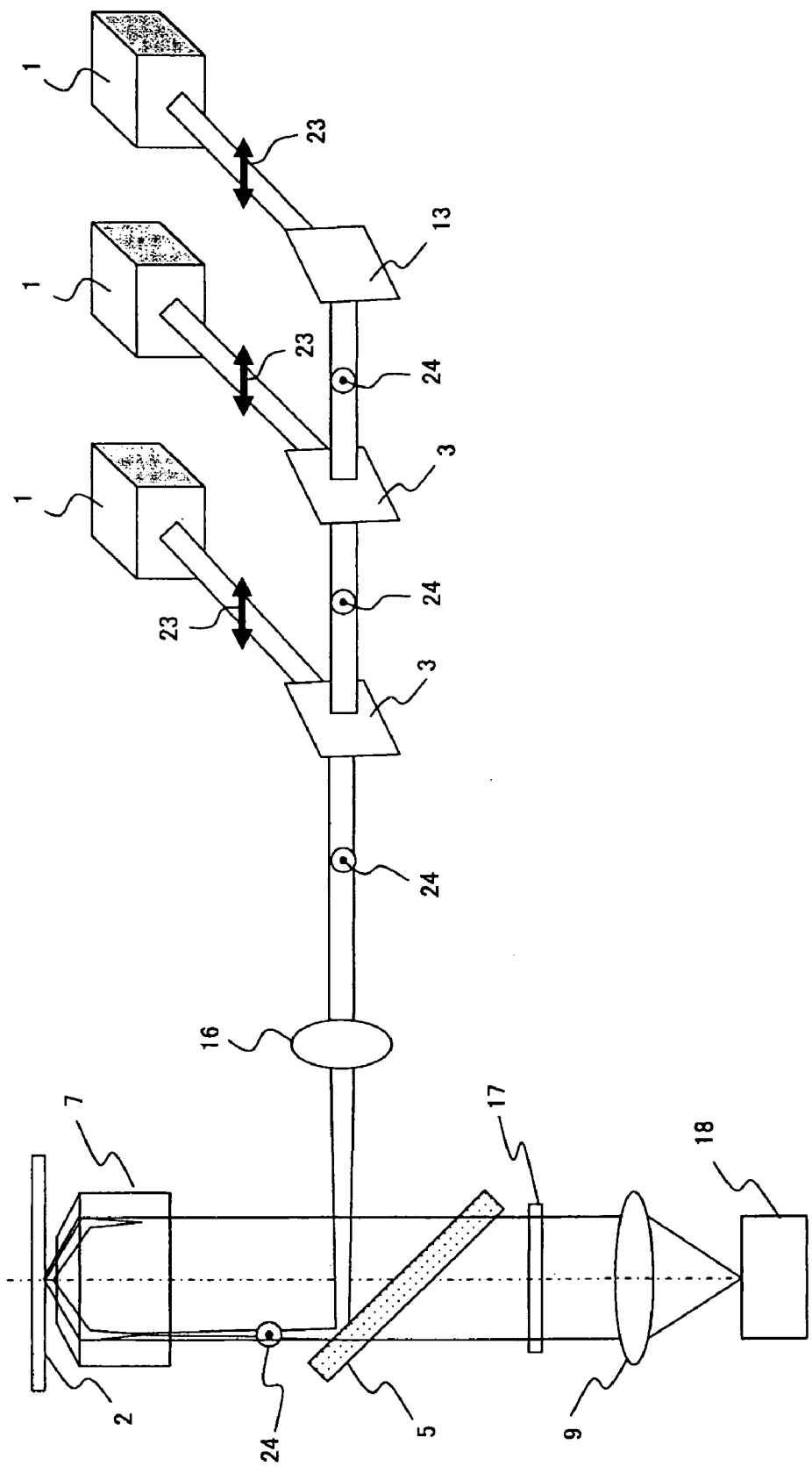
FIG. 3 shows the outline of the configuration of the TIRF (Total Internal Reflection Fluorescence) microscope according to an embodiment of the present invention.

FIG. 3 shows the outline of an example of the configuration of the TIRF (total internal reflection fluorescence) microscope as the optical equipment embodying the present invention. A TIRF microscope is a fluorescent microscope for emitting excitation light only to (a part of) a sample near a cover glass by using the phenomenon of the total reflection by the cover glass loaded with the sample. The used excitation light is laser beams in many cases, and the optical equipment is desired as an embodiment of the present invention.

The TIRF microscope according to the present embodiment is configured by the laser beam sources 1 for emitting laser beams, the dichroic mirror 3 for combining the laser beams, an illumination optical system 16 for appropriately converging the laser beams, the plane-parallel plate glass 5 for reflecting the laser beams and introducing them to a detection optical path, a fluorescent filter 17 for passing only desired fluorescence from among the beams passing through the plane-parallel plate glass 5, the tube lens 9 for forming an image from the beams obtained from a sample in cooperation with the objective lens 7, and an image pickup element 18 arranged at the back focal position of the tube lens 9. The mirror 13 shown in FIG. 3 is used to appropriately arrange the optical path.

With the above-mentioned configuration, the laser beams from the laser beam sources 1 enter the dichroic mirror 3 as P polarization, and pass through and are reflected by the dichroic mirror 3. Thus, the laser beams from the plurality of laser beam sources 1 are combined into a bundle of laser beams. Afterwards, the combined laser beams are converged to be condensed at the back focal position of the objective lens 7 at the subsequent stage by the illumination optical system 16. Furthermore, the laser beams passing through the illumination optical system 16 enter the plane-parallel plate glass 5 as S polarization. The plane-parallel plate glass 5 reflects the laser beams, and leads the reflected light towards the objective lens 7. At this time, the laser beams do not enter to fill the pupil of the objective lens 7, but enter close to the perimeter of the pupil. The beams emitted to a sample from the outside of the range of the pupil of the objective lens 7 enter the cover glass at an angle larger than the total reflection angle determined by the difference in refractive index between a sample and the cover glass for supporting the sample. With the configuration, only the evanescent light is allowed to reach the sample in the illustrating method. To suppress the total reflection on the points other than the point between the cover glass and the sample, the objective lens 7 with the configuration can be an oil immersion objective. That is, oil having a predetermined refractive index is filled between the objective lens 7 and the cover glass.

The fluorescence in the sample excited by the evanescent light is converted into parallel luminous flux by an objective lens. Furthermore, the fluorescence is formed as an image on the acceptance surface of the image pickup element 18 by the tube lens 9. At this time, it is desired to have the configuration of providing the fluorescent filter 17 for passing only the wavelength of the desired fluorescence between the plane-parallel plate glass 5 and the tube lens 9.

In the observation using the evanescent light, there is a request to change the direction of polarization of the laser beams entering the sample surface 2. In this case, the reflection position on the plane-parallel plate glass 5 can be changed. Then, the polarization surface in the sample surface 2 can be rotated while holding the S polarization on the plane-parallel plate glass 5. In addition, the polarization surface of the laser beams can also be rotated by inserting a λ/2 plate between the plane-parallel plate glass 5 and the objective lens 7.

With the configuration of the present embodiment, it is preferable to make devices by changing the thickness and refractive index of the plane-parallel plate glass 5, adding a wedge and a reflection preventive coat to the plane-parallel plate glass 5, etc. Since practical configurations are the same as in the embodiment 1, the explanation is omitted here.

Embodiment 3

Figure 4:
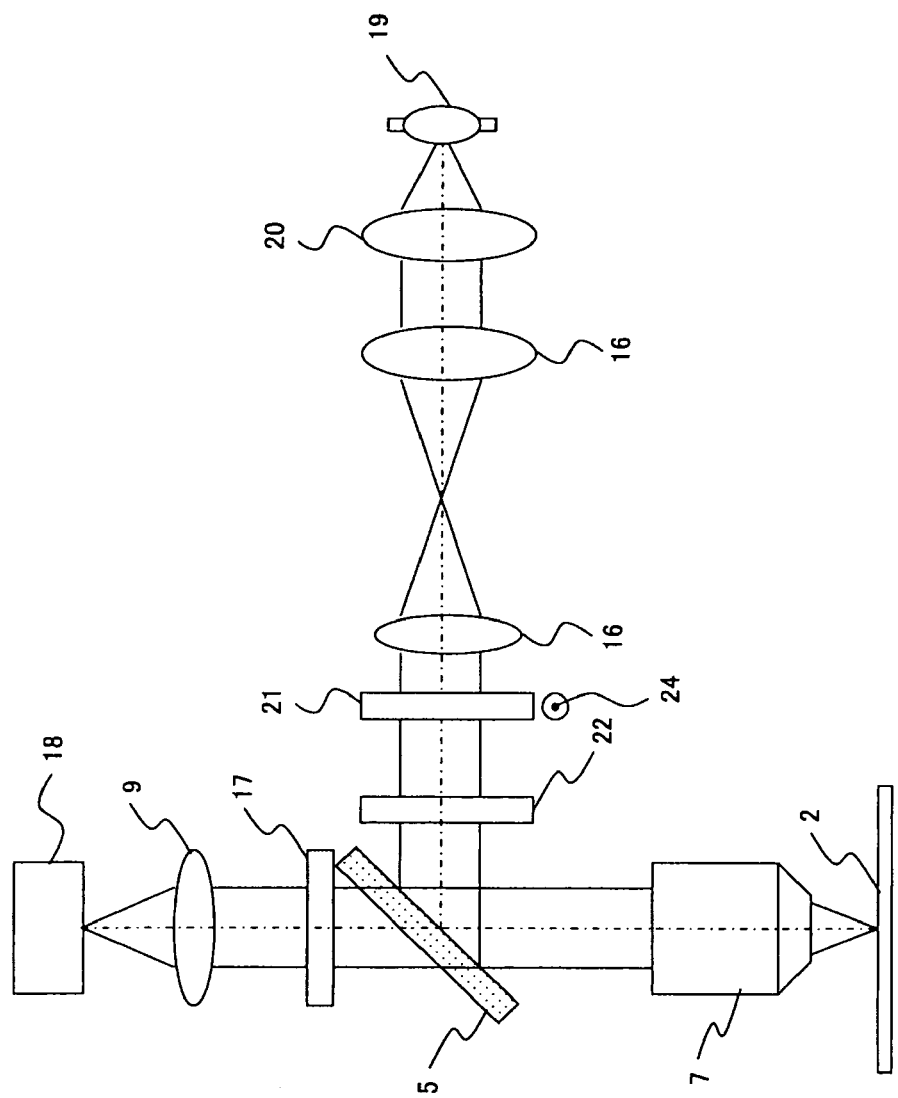
FIG. 4 shows the outline of the coaxial incident-light fluorescent microscope according to an embodiment of the present invention.

FIG. 4 shows the outline of an example of the configuration of the coaxial incident-light fluorescent microscope as optical equipment embodying the present invention. In a common coaxial incident-light fluorescent microscope, laser beams are not used as a light source, but a light source of an arc light source etc. That is, with the configuration, since a light source itself does not emit linear polarization, a polarizing plate is inserted into an illumination optical path. Thus, the illumination light becomes linear polarization, thereby realizing the present invention. For example, a polarized fluorescence observation etc. with a coaxial incident-light fluorescent microscope is an example of an application of the present embodiment.

The present embodiment is configured by a light source 19 for emitting illumination light, a collector lens 20 for converting illumination light emitted from the light source 19 into a substantially parallel luminous flux, the illumination optical system 16 for appropriately introducing the illumination light to the pupil of an objective lens, a polarizing plate 21 for converting the illumination light to linear polarization, a exciter filter 22 for selecting beams of a desired excitation wavelength from the illumination light, the plane-parallel plate glass 5 for reflecting the linear polarization and introducing reflected light to a detection optical path, the objective lens 7 for irradiating a sample with the illumination light and fetching fluorescence, the fluorescent filter 17 for passing only the beams of a desired wavelength from among the beams passing through the plane-parallel plate glass 5, the tube lens 9 for image forming the beams from the sample in cooperation with the objective lens 7, and the image pickup element 18 arranged at the back focal position of the tube lens 9.

With the configuration, the illumination light emitted from the light source 19 is converted into a substantially parallel luminous flux by the collector lens 20. Furthermore, the illumination light is adjusted to form an image of the light source 19 at the back focal position of the objective lens 7. Afterwards, the illumination light enters the plane-parallel plate glass 5, and the reflected light is led to the objective lens 7. At this time, the polarizing plate 21 is mounted in the optical path between the light source 19 and the plane-parallel plate glass 5 such that the illumination light can enter the plane-parallel plate glass 5 as the S polarization.

It is also preferable that the exciter filter 22 for selecting a desired excitation wavelength is mounted in the optical path between the light source 19 and the plane-parallel plate glass 5. In FIG. 4, the exciter filter 22 is arranged in the position close to the plane-parallel plate glass 5. However, in addition to this arrangement, the exciter filter 22 can be arranged in the optical path between the light source 19 and the plane-parallel plate glass 5. In the typical coaxial incident-light fluorescent microscope, the exciter filter 22, the fluorescent filter 17, and the dichroic mirror (not used in the present embodiment) are configured in a unitary construction, and is simultaneously exchanged. When the unit referred to as a fluorescence cube is applied, the exciter filter 22, the fluorescent filter 17, and the plane-parallel plate glass 5 can be preferably configured as a unit. However, the plane-parallel plate glass 5 used in the present embodiment is substantially wavelength-independent. Therefore, it is not necessary to exchange the plane-parallel plate glass 5 together with the exciter filter 22. As a result, in the present embodiment, the flexibility of the arrangement of the exciter filter 22 is improved, and the exciter filter 22 can be provided with a motor-driven filter wheel etc. and arranged in an optional position.

The linear polarization reflected by the plane-parallel plate glass 5 excites the fluorescence substance in the sample through the objective lens 7. The excited fluorescence substance emits fluorescence. The emitted fluorescence passes through the plane-parallel plate glass 5. Only the beams of a desired wavelength are selected by the fluorescent filter 17 from the fluorescence that has passed through the plane-parallel plate glass 5, and are image-formed on the acceptance surface of the image pickup element 18.

The emitted fluorescence is frequently random polarization, but can inherit the characteristic of polarization which is exciting light. The phenomenon occurs when the fluorescence substance has a heavier molecule weight while the molecular action is low. The phenomenon is measured in a polarization fluorescence observation. When the configuration is used in the polarization fluorescence observation, the difference in refractive index between the P polarization and the S polarization of the plane-parallel plate glass 5 (that is, the different in transmittance) affects detection. However, the influence can be corrected by measuring in advance the characteristic of the plane-parallel plate glass 5. In the polarized fluorescence observation, a polarization beam splitter is arranged between the fluorescent filter 17 and the tube lens 9 to separate the P polarization from the S polarization for detection.

With the configuration of the present embodiment, it is desired that a reflection preventive coat is applied to the plane-parallel plate glass 5. Since a practical example is similar to the configuration in the embodiment 1, the explanation is omitted here.

What is claimed is:

1. An optical equipment which detects beams emitted from a sample by irradiating the sample with linear polarization, the optical equipment comprising:
   a wavelength-independent optical path division element arranged at a position of coupling of an illumination optical path of the linear polarization and a detection optical path of the beams, wherein the optical path division element comprises an optical glass non-coated on both faces thereof;
   wherein the linear polarization, which enters as S polarization, is reflected by an interface of the optical path division element and led to the sample; and
   wherein the beams, which are randomly-polarized, are emitted from the sample, pass through the optical path division element, and are detected.

2. The optical equipment according to claim 1, wherein the optical path division element is a plane-parallel plate glass.

3. The optical equipment according to claim 2, wherein the following inequality for a thickness D of the plane-parallel plate glass holds $$D > A(n^2 - 0.5)^{1/2}$$

where A indicates a luminous flux diameter of the linear polarization, and n indicates a refractive index of the plane-parallel plate glass.

4. The optical equipment according to claim 3, wherein:
   the linear polarization has a Gaussian intensity distribution; and
   the luminous flux diameter A is regulated as a beam diameter having intensity of $1/e^2$ relative to a central intensity of the linear polarization.

5. The optical equipment according to claim 3, wherein the luminous flux diameter A is regulated as a diameter of an iris arranged at a stage before the plane-parallel plate glass.

6. The optical equipment according to claim 1, further comprising:
   an objective lens arranged close to the sample; and
   a tube lens which forms an image from beams emitted from the objective lens,
   wherein the optical path division element is arranged between the objective lens and the tube lens.

7. The optical equipment according to claim 6, wherein the linear polarization is generated by illumination light emitted from a light source passing through a polarizing plate.

8. The optical equipment according to claim 6, wherein the linear polarization comprises laser beams emitted from a laser light source; and
wherein the laser beams enter only near a perimeter of a pupil of the objective lens.

9. The optical equipment according to claim 1, further comprising:
an objective lens arranged close to the sample;
a tube lens which forms an image from beams emitted from the objective lens;
a pupil projection lens which relays beams emitted from the tube lens and which projects a pupil of the objective lens;
a scanning device arranged in a position of the pupil projected by the pupil projection lens; and
a detector which detects the beams emitted from the sample by the scanning device scanning the sample using the linear polarization,
wherein the optical path division element is arranged between the scanning device and the detector.

10. The optical equipment according to claim 9, wherein:
the linear polarization comprises laser beams emitted from laser diodes; and
a polarization surface of the linear polarization matches a direction of a major axis of a section of each of the laser beams.

11. The optical equipment according to claim 1, wherein the randomly-polarized beams comprise fluorescent light emitted from a fluorescent material in the sample.

12. The optical equipment according to claim 1, wherein the optical equipment is a laser scanning microscope.

13. An optical equipment which detects beams emitted from a sample by irradiating the sample with linear polarization, the optical equipment comprising:
a wavelength-independent optical path division element arranged at a position of coupling of an illumination optical path of the linear polarization and a detection optical path of the beams, wherein the optical path division element comprises an optical glass including a non-coated incident face where the linear polarization enters, and a face which is mounted opposite to the non-coated incident face and which is covered with a reflection preventive coating;
wherein the linear polarization, which enters as S polarization, is reflected by the non-coated incident face of the optical path division element and led to the sample; and
wherein the beams, which are randomly-polarized, are emitted from the sample, pass through the optical path division element, and are detected.

14. The optical equipment according to claim 13, wherein the optical path division element is a plane-parallel plate glass.

15. The optical equipment according to claim 14, wherein the following inequality for a thickness D of the plane-parallel plate glass holds $$D > A(n^2 - 0.5)^{1/2}$$

where A indicates a luminous flux diameter of the linear polarization, and n indicates a refractive index of the plane-parallel plate glass.

16. The optical equipment according to claim 15, wherein:
the linear polarization has a Gaussian intensity distribution; and
the luminous flux diameter A is regulated as a beam diameter having intensity of $1/e^2$ relative to a central intensity of the linear polarization.

17. The optical equipment according to claim 15, wherein the luminous flux diameter A is regulated as a diameter of an iris arranged at a stage before the plane-parallel plate glass.

18. The optical equipment according to claim 13, further comprising:
an objective lens arranged close to the sample; and
a tube lens which forms an image from beams emitted from the objective lens,
wherein the optical path division element is arranged between the objective lens and the tube lens.

19. The optical equipment according to claim 18, wherein the linear polarization is generated by illumination light emitted from a light source passing through a polarizing plate.

20. The optical equipment according to claim 18, wherein the linear polarization is laser beams emitted from a laser light source; and
wherein the laser beams enter only near a perimeter of a pupil of the objective lens.

21. The optical equipment according to claim 13, further comprising:
an objective lens arranged close to the sample;
a tube lens which forms an image from beams emitted from the objective lens;
a pupil projection lens which relays beams emitted from the tube lens and which projects a pupil of the objective lens;
a scanning device arranged in a position of the pupil projected by the pupil projection lens; and
a detector which detects the beams emitted from the sample by the scanning device scanning the sample using the linear polarization,
wherein the optical path division element is arranged between the scanning device and the detector.

22. The optical equipment according to claim 21, wherein:
the linear polarization comprises laser beams emitted from laser diodes; and
a polarization surface of the linear polarization matches a direction of a major axis of a section of each of the laser beams.

23. The optical equipment according to claim 13, wherein the randomly-polarized beams comprise fluorescent light emitted from a fluorescent material in the sample.

24. The optical equipment according to claim 13, wherein the optical equipment is a laser scanning microscope.

* * * * *